(12) United States Patent
Jeong et al.

(10) Patent No.: US 12,165,626 B2
(45) Date of Patent: Dec. 10, 2024

(54) ULTRASONIC LENS ANDULTRASONIC WAVE EMITTING DEVICE HAVING THE SAME

(71) Applicants: KOREA INSTITUTE OF MACHINERY & MATERIALS, Daejeon (KR); CENTER FOR ADVANCED META-MATERIALS, Daejeon (KR)

(72) Inventors: Jun-Ho Jeong, Daejeon (KR); Hyeokjung Kang, Daejeon (KR); Sohee Jeon, Seoul (KR); Soon-Hyoung Hwang, Daejeon (KR); Yongrok Jeong, Daejeon (KR)

(73) Assignees: KOREA INSTITUTE OF MACHINERY & MATERIALS, Daejeon (KR); CENTER FOR ADVANCED META-MATERIALS, Daejeon (KR)

( * ) Notice: Subject to any disclaimer, the term of this patent is extended or adjusted under 35 U.S.C. 154(b) by 322 days.

(21) Appl. No.: 17/711,295

(22) Filed: Apr. 1, 2022

(65) Prior Publication Data
US 2022/0319490 A1 Oct. 6, 2022

(30) Foreign Application Priority Data
Apr. 2, 2021 (KR) ........................ 10-2021-0043259

(51) Int. Cl.
*G10K 11/30* (2006.01)
*A61B 8/00* (2006.01)
*G01N 29/22* (2006.01)

(52) U.S. Cl.
CPC ............ *G10K 11/30* (2013.01); *A61B 8/4444* (2013.01); *G01N 29/221* (2013.01)

(58) Field of Classification Search
CPC . A61N 2007/027; G10K 11/30; A61B 8/4444
See application file for complete search history.

(56) References Cited

U.S. PATENT DOCUMENTS

| 4,622,972 A | * | 11/1986 | Giebeler, Jr. | ............ A61N 7/02 601/3 |
| 6,274,917 B1 | * | 8/2001 | Fan | ................... H01L 27/14609 257/233 |
| 2020/0412009 A1 | * | 12/2020 | Borrelli | .............. H01Q 21/0031 |

FOREIGN PATENT DOCUMENTS

KR 10-1294292 B1 8/2013

OTHER PUBLICATIONS

S. Perez-Lopez et al., "Bifocal Ultrasound Focusing Using Bi-Fresnel Zone Plate Lenses", Sensors, vol. 2, No. 705, pp. 1-9, Jan. 2020 (Year: 2020).*

(Continued)

*Primary Examiner* — Joel Lamprecht
*Assistant Examiner* — Nyrobi Celestine
(74) *Attorney, Agent, or Firm* — Hauptman Ham, LLP

(57) ABSTRACT

In a wave focusing device and a wave emitting device having the wave focusing device, the wave focusing device has a plurality of filters and focuses a wave by a phase overlap. The plurality of filters includes a first filter formed on a substrate, a second filter formed on the substrate and overlapping with the first filter in a first area, and a third filter formed on the substrate and overlapping with the second filter in a second area. A size of the first area is substantially same as that of the second area. A first portion of the second filter in the first area is inverted to a second portion of the second filter in the second area, with respect to a first axis. A wave passing through the wave focusing device is focused at a center of each of the first, second and third filters.

20 Claims, 4 Drawing Sheets

(56) References Cited

OTHER PUBLICATIONS

B. Huang et al., "Multifocal co-plane metalens based on computer-generated holography for multiple visible wavelengths", Physics, vol. 17, pp. 1-6, Mar. 2020 (Year: 2020).*

* cited by examiner

ULTRASONIC LENS AND ULTRASONIC WAVE EMITTING DEVICE HAVING THE SAME

This application claims priority under 35 U.S.C. § 119 to Korean Patent Application No. 10-2021-0043259, filed on Apr. 2, 2021, the disclosure of which is incorporated by reference herein in its entirety.

BACKGROUND

1. Field of Disclosure

The present disclosure of invention relates to a wave focusing device and a wave emitting device having the wave focusing device, and more specifically the present disclosure of invention relates to a wave focusing device and a wave emitting device having the wave focusing device, in which a multifocal design method is used for increasing focusing of a wave in a predetermined area and a plurality of filters is overlapped with each other to control a focal length.

2. Description of Related Technology

In wave focusing technology through phase overlap, a phase to a focus is set for a wave at which diffraction occurs, to increase the wave focusing. The above technology is called as lens effect, and the wave focusing is increased in a predetermined area but the wave focusing is hard to be controlled in an area except for the predetermined area.

The lens effect may be maximized by using a Fresnel zone plate filter. However, since the area of the filter is extremely larger than the focusing area, the increase of the wave focusing is limited in the entire area, even though the lens is formed with a relatively narrow size. Thus, the technology for increasing the wave focusing in the entire area near a surface, and minimizing an interference between the focuses is required.

Related prior art is Korean Patent No. 10-1294292.

SUMMARY

The present invention is developed to solve the above-mentioned problems of the related arts.

The present invention provides a wave focusing device providing a multifocal design method capable of increasing the wave focusing in an entire area near a surface.

In addition, the present invention also provides a wave focusing device capable of increasing the entire wave focusing near the surface, by cutting an arc into pieces and placing the pieces.

In addition, the present invention also provides a wave focusing device capable of increasing the entire wave focusing at a position corresponding to a center of a filter, by overlapping a plurality of filters with each other.

In addition, the present invention also provides a wave focusing device capable of controlling a focal distance by overlapping a plurality of filters with each other, and capable of supplementing the controlled focal distance by additional spacers.

In addition, the present invention also provides a wave emitting device having the wave focusing device.

According to an example embodiment, wave focusing device has a plurality of filters and focuses a wave by a phase overlap. The plurality of filters includes a first filter formed on a substrate, a second filter formed on the substrate and overlapping with the first filter in a first area, and a third filter formed on the substrate and overlapping with the second filter in a second area. A size of the first area is substantially same as that of the second area.

In an example, a first portion of the second filter in the first area is inverted to a second portion of the second filter in the second area, with respect to a first axis. A wave passing through the wave focusing device is focused at a center of each of the first, second and third filters.

In an example, the shapes of the first, second and third filters may be substantially same with each other.

In an example, the wave passing through the wave focusing device may have a plurality of focuses, and the number of the focuses may correspond to the number of the filters.

In an example, each of the first, second and third filters may be a Fresnel zone plate filter.

In an example, a shape of a third portion of the first filter in the first area may be substantially same as that of the second portion.

According to another example embodiment, a wave emitting device has a plurality of focuses. The wave emitting device includes a wave emitter configured to emit a wave, a first spacer configured to stabilize the wave emitted from the wave emitter, a wave focusing lens configured to focus the wave emitted from the first spacer, and a second spacer configured to receive the wave emitted from the wave focusing lens. The second space has a first length, and the first length is shorter than a focal distance of the wave. The wave focusing lens has a plurality of filters formed on a substrate, and the areas in which the filters are formed are overlapped with each other.

In an example, the wave focusing lens may include a first filter, a second filter overlapping with the first filter in a first area, and a third filter overlapping with the second filter in a second area. A size of the first area may be substantially same as that of the second area.

In an example, each of the focuses may correspond to a center of each of the first, second and third filters.

In an example, the wave emitting device may emit the wave to a first surface. The first length may be determined based on a distance between the wave focusing lens and the first surface, and the focal distance of the wave.

In an example, the plurality of the filters of the wave focusing lens may have the shape substantially same with each other.

According to the present example embodiments, the plurality of filters is overlapped with each other, to increase the wave focusing in the entire area near the surface.

In addition, the wave focusing is increased at the position corresponding to the center of each of the filters.

In addition, the plurality of filters is used, to pull the focal distance, compared that a single filter is used.

Figure 1:
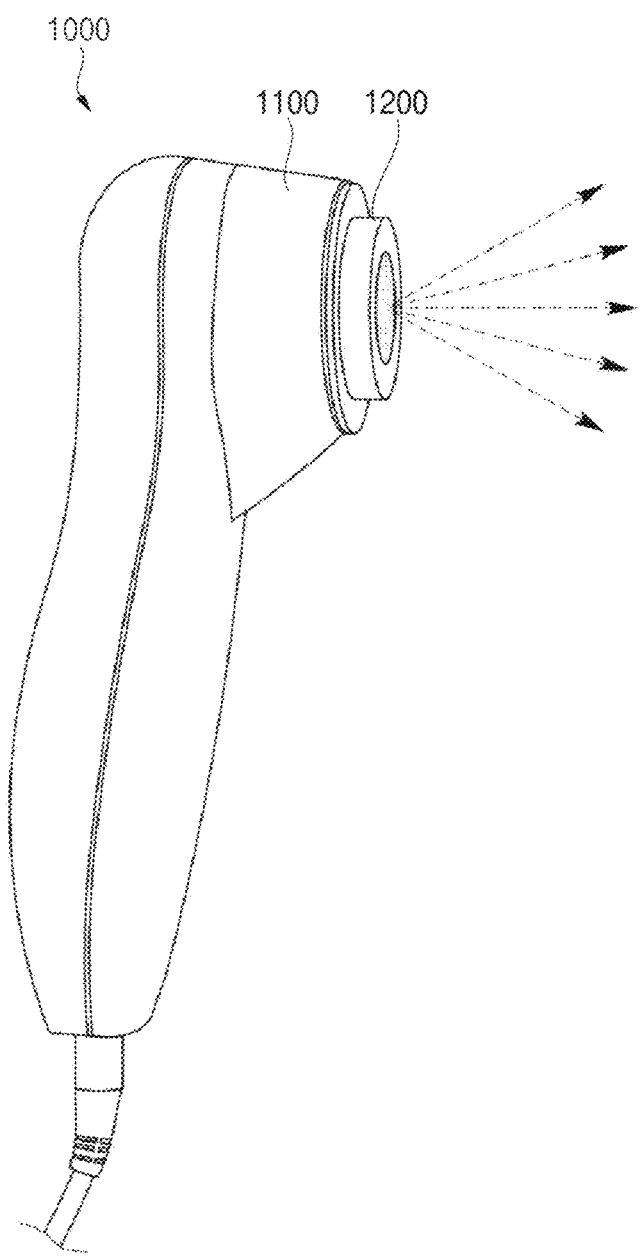
FIG. 1 is a perspective view illustrating a wave emitting device according to an example embodiment of the present invention.

| * Reference numerals | |
|---|---|
| 1000: wave emitting device | 1100: body |
| 1200: emitting part | 300: wave focusing lens (device) |
| 310: first filter | 320: second filter |
| 330: third filter | 340: first area |
| 350: second area | 360: first axis |

DETAILED DESCRIPTION

The invention is described more fully hereinafter with Reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. In the drawings, the size and relative sizes of layers and regions may be exaggerated for clarity.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The photocatalytic facial mask (hereinafter, the facial mask) according to the present example embodiments of the present invention may solve the temporal and spatial constraints of photocatalytic activity of the conventional mask having the photocatalyst, may have excellent photocatalytic activity, may be easy to be cleaned and may be used with plural times.

Here, in the facial mask according to the present example embodiments, a functional filter layer is disposed between an inner layer and an outer layer of the facial mask, and the functional filter layer includes a photoactive layer which includes a photocatalytic fiber having a core-shell structure.

Hereinafter, the invention is described more fully hereinafter with reference to the accompanying drawings, in which embodiments of the invention are shown.

FIG. 1 is a perspective view illustrating a wave emitting device according to an example embodiment of the present invention.

Referring to FIG. 1, the wave emitting device 1000 according to the present example embodiment includes a body 1100 and an emitting part 1200.

The body 1100 may include a power, an intensity control part and a controller. The power is configured to control an operation of emitting of a wave, and the intensity control part is configured to control an intensity of the wave. The controller is configured to control all operation of the body 1100.

The power controls a power source of a wave emitter to control an On/Off of the emitting of the wave. The intensity control part controls a voltage of the waver emitter to control the intensity of the wave.

The wave emitting device 1000 may irradiate an ultrasonic wave to a skin. Here, a focal distance of the ultrasonic wave from the wave emitting device 1000 is controlled to be focused between the epidermis and the dermis, to have a remarkable effect on the treatment of the skin and the beauty.

In the conventional wave emitting device, the emitted ultrasonic wave has the focal distance disposed in a subcutaneous tissue under the dermis, and the ultrasonic wave having relatively high intensity and energy is irradiated to the subcutaneous tissue, so that the problems that results in skin diseases such as a skin cancer may exist.

Figure 3:
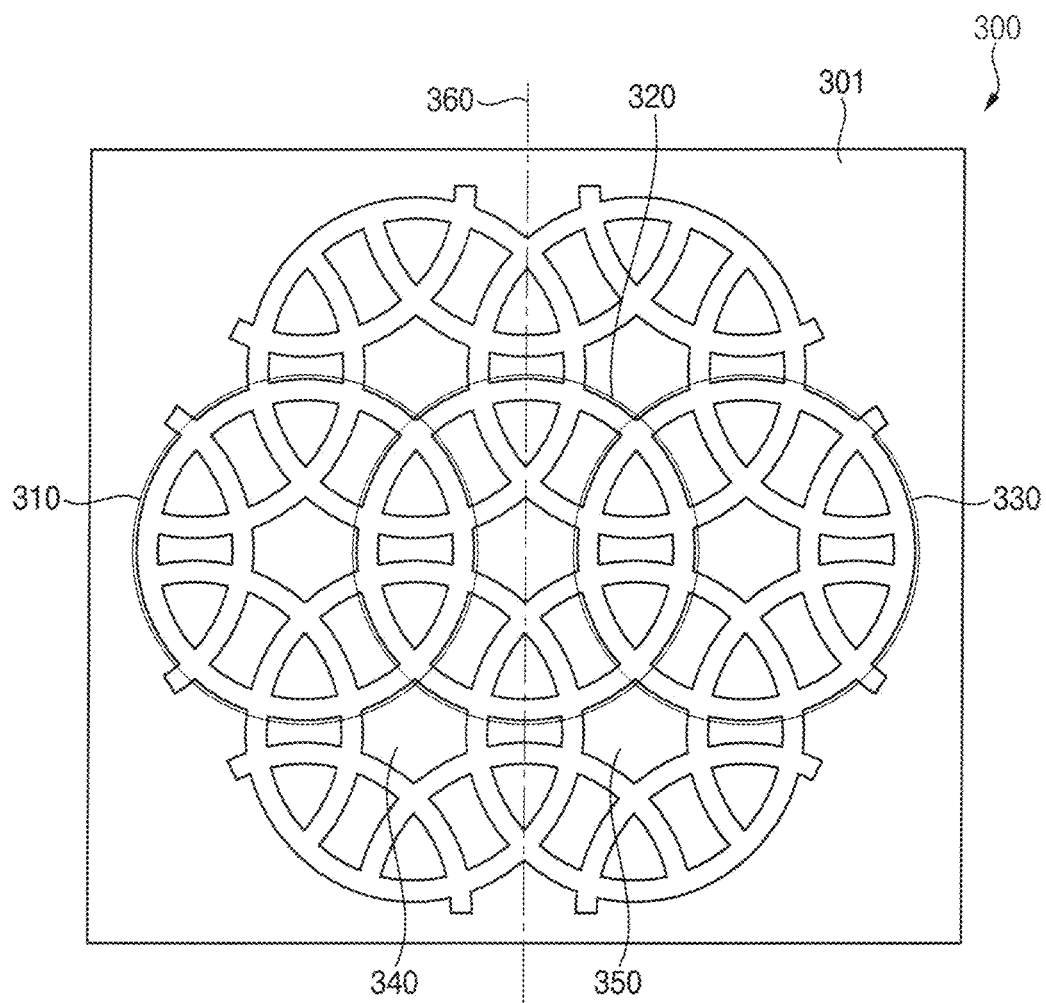
FIG. 3 is a plan view illustrating a wave focusing device of FIG. 2.

However, in the wave emitting device 1000 according to the present example embodiment, the focal distance is pulled by using a wave focusing lens of FIG. 3, compared to the conventional wave emitting device, and thus the focal distance of the emitted ultrasonic wave is disposed between the epidermis and the dermis. Thus, a therapeutic and/or cosmetic purpose of the skin may be achieved, and the risk of skin diseases may be greatly reduced.

In addition, when the ultrasonic wave is generated with making the wave emitting device 1000 contact with a microneedle patch attached to the skin, the temperature between the epidermis and the dermis is increased and a micro-cavity is formed. As the temperature inside of the skin increases, the soluble microneedle is dissolved faster and a drug release rate is increased, and then the released drug is absorbed faster by the micro-cavity formed inside of the skin. Here, a drug penetration effect of the wave emitting device 1000 may be increased.

The emitting part 1200 of the wave emitting device 1000 controls a focal distance of the emitted wave, by using the wave focusing lens, to locate a focus of the wave between the epidermis and the dermis.

For example, when a distance from the wave focusing lens to the focus of the wave is 4 mm and a depth of the epidermis of the skin is 1 mm, the length of the emitting part 1200 is formed to be 3 mm so that the focal distance may be controlled.

The emitting part 1200 includes a material easily transmitting the wave and not irritating the skin. For example, the emitting part 1200 may include a transparent rubber or a gel, but not limited thereto.

Figure 2:
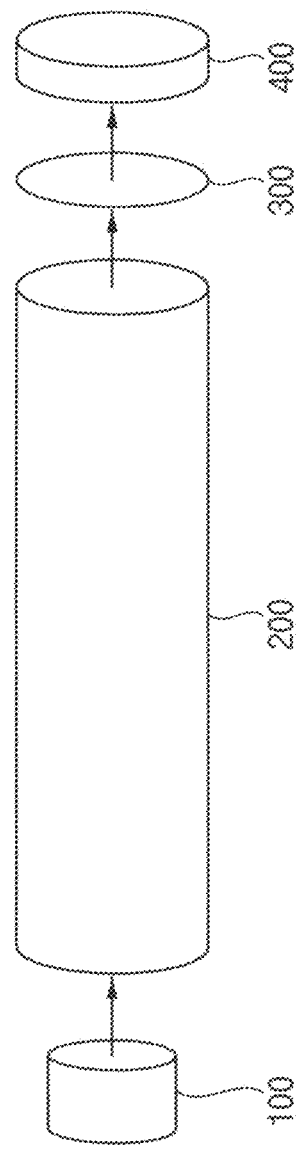
FIG. 2 is an exploded perspective view illustrating the wave emitting device of FIG. 1.

FIG. 2 is an exploded perspective view illustrating the wave emitting device of FIG. 1.

Referring to FIG. 2, the wave emitting device 1000 according to the present example embodiment further includes a wave emitter 100, a first spacer 200, a wave focusing lens 300 and a second spacer 400.

The controller of the wave emitting device 1000 applies a voltage to the wave emitter 100, and then the wave emitter 100 emits the wave. For example, the wave emitter 100 may emit the ultrasonic wave having a wavelength more than about 20,000 Hz, and more specifically about 1.7 MHz or about 1 MHz. In addition, an intensity of the wave emitted from the wave emitter 100 may be controlled by the intensity control part of the wave emitting device 1000.

The first spacer 200 receives the wave emitted from the wave emitter 100. The first spacer 200 stabilizes the received wave. The first spacer 200 have a length longer than that of the second spacer 400, so that the wave emitted from the wave emitter 100 passes through the first spacer 200 and then is stabilized.

Here, the first spacer 200 may include a material easily transmitting the wave, such as a transparent rubber or a gel, but not limited thereto.

The wave focusing lens 300 receives the wave emitting from the first spacer 200. The wave focusing lens 300 pulls the focal distance of the received wave. For example, the focal distance of the wave emitted from the first spacer 200 is 4 mm, but the focal distance of the wave passing through the wave focusing lens 300 may be pulled into 1 mm Here, the pulled value may be not limited thereto, and the pulled focal distance may be changed according to a kind of the lens.

A shape and a configuration of the wave focusing lens 300 are explained referring to FIG. 3 in detail.

The second spacer 400 receives the wave emitted from the wave focusing lens 300. The second spacer 400 supplements the focal distance pulled by the wave focusing lens 300, to locate the focus of the received wave between the epidermis and the dermis. Thus, a length of the second spacer 400 may be determined based on a distance between the wave focusing lens 300 and the skin (the epidermis and the dermis), and the focal distance of the wave.

The second spacer 400 may be the emitting part 1200 of FIG. 1. The second spacer 400 may include a material easily transmitting the wave and not irritating the skin, like the material of the first spacer 200 and the emitting part 1200. For example, the second spacer 400 may include a transparent rubber or a gel, but not limited thereto.

FIG. 3 is a plan view illustrating a wave focusing device of FIG. 2.

Referring to FIG. 3, the wave focusing device of FIG. 3 may be the wave focusing lens 300 of FIG. 2, and thus the wave focusing device may be referred or called as the wave focusing lens or an ultrasonic lens, hereinafter.

The wave focusing lens 300 includes a plurality of filters formed on a substrate 301, for example a stainless steel plate. Here, the wave focusing lens 300 may include a Fresnel zone plate filter, but not limited thereto, and may include various kinds of filters focusing the wave. The filters included in the wave focusing lens 300 may be a circular shape filter as illustrated in FIG. 3, but not limited thereto, and may have various kinds of shapes such as an elliptical shape, a polygon shape and so on.

The shape in FIG. 3 is formed by perforating the substrate 301, and the shape is a hole formed through the substrate 301. The wave passes through the hole of the wave focusing lens 300, and then phases of the wave overlap with each other. The wave passes through the hole of the plurality of the filters included in the wave focusing lens 300, and then a multi-focus may be formed by the phase overlapping.

In addition, compared to the focal distance of the wave focusing lens having a single filter, the focal distance of the wave focusing lens 300 according to the present example embodiment having the plurality of the filters overlapped with each other is shorter, and thus the focal distance may be pulled.

Here, the wave focusing lens 300 may include a first filter 310, a second filter 320 and a third filter 330 formed through the substrate 301. The filters of the wave focusing lens 300 may partially overlap with each other. In addition, the plurality of the filters of the wave focusing lens 300 may have the same shape and structure with each other.

The first filter 310 partially overlaps with the second filter 320 in a first area 340, and the second filter 320 partially overlaps with the third filter 330 in a second area 350. Here, a size of the first area 340 is substantially same as a size of the second area 350, and further a shape of the first area 340 may be also substantially same as the shape of the second area 350.

A portion of the first filter 310 included in the first area 340 is substantially same as a portion of the second filter 320 included in the second area 350. In addition, a portion of the second filter 320 included in the first area 340 is substantially same as a portion of the third filter 330 included in the second area 350.

In addition, a portion of the first and second filters 310 and 320 included in the first area 340 is substantially same as a portion of the second and third filters 320 and 330 included in the second area 350.

In addition, the portion of the second filter 320 included in the first area 340 is inverted to the portion of the second filter 320 included in the second area 350, with respect to a first axis 360. Here, the first axis 360 is an axis passing through a center of the second filter 320.

The wave passing through the wave focusing lens 300 may have a plurality of focuses and the number of the focuses may be the same as the number of the filters included in the wave focusing lens 300.

In addition, the focuses of the wave passing through the wave focusing lens 300 may be located at the centers of the filters of the wave focusing lens 300, respectively. For example, the positions of the focuses are respectively same as the centers of the filters, or the positions thereof and the centers thereof may be spaced apart from each other by the same distance, when the wave emitting device 1000 is viewed in a front side along a direction in which the wave is emitted.

The filters included in the wave focusing lens 300 may overlap with at least two filters. For example, six filters around the second filter 320 may partially overlap with the second filter 320 as illustrated in FIG. 3, and the number of the filters overlapping with the second filter 320 may be changed according to the shape or the structure of the filter.

That is, as illustrated in FIG. 3, when each of the filters has a circular shape, six circular filters around the specific circular filter (for example the second filter 320) partially overlap with the specific circular filter. Here, the filters around the specific filter (for example, the second filter 320) are spaced apart from each other by a constant arc length. Thus, the wave focusing lens 300 has the shape and structure illustrated in FIG. 3.

Figure 4:
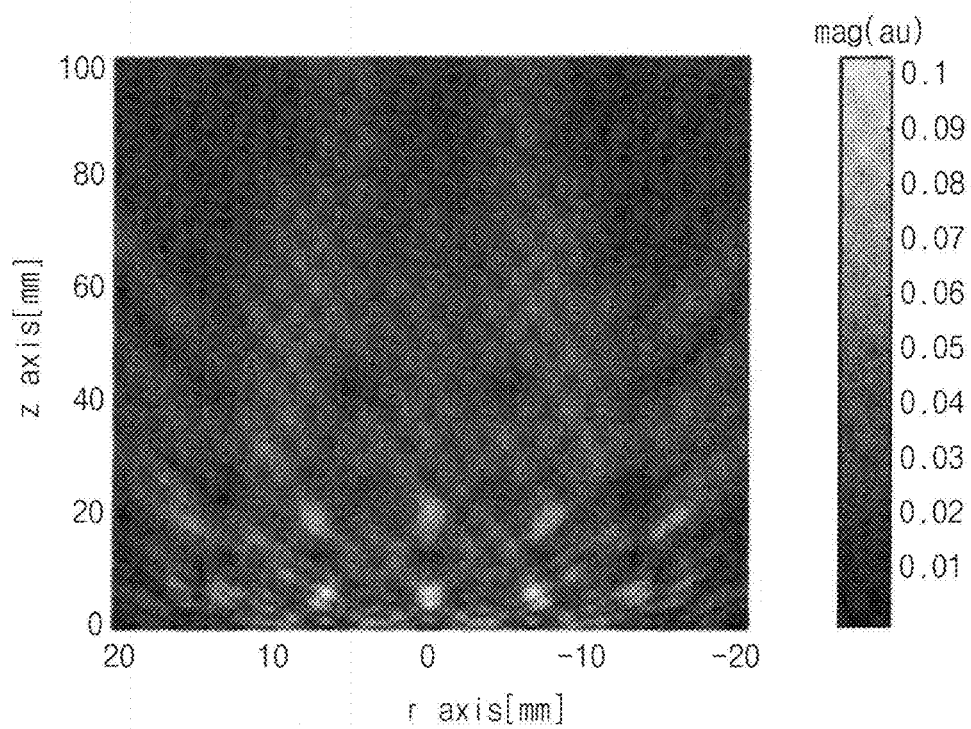
FIG. 4 is an image showing a shape of the wave focused by the wave focusing device of FIG. 3.

FIG. 4 is an image showing a shape of the wave focused by the wave focusing device of FIG. 3.

Referring to FIG. 4, the wave passing through the wave focusing lens 300 has the focuses at multiple positions.

For example, the wave passing through the wave focusing lens 300 may have the focuses at the positions of about −7, about 0 and about 7 along an r axis of the graph of FIG. 4. In addition, the wave passing through the wave focusing lens 300 may have the focuses at the positions of about 5 and about 20 along a z axis of the graph of FIG. 4. Here, the separated distance between the focuses may be the same in FIG. 4 in the wave focusing lens 300 of the present example embodiment.

As illustrated in FIG. 4, the wave emitting device of the present example embodiment is designed to have the multifocal design method, to increase the focusing of the wave at a predetermined distance, and has the filters having the patterns to minimize the interference of the focuses, so that multifocal surface focusing wave may be emitted.

Figure 5:
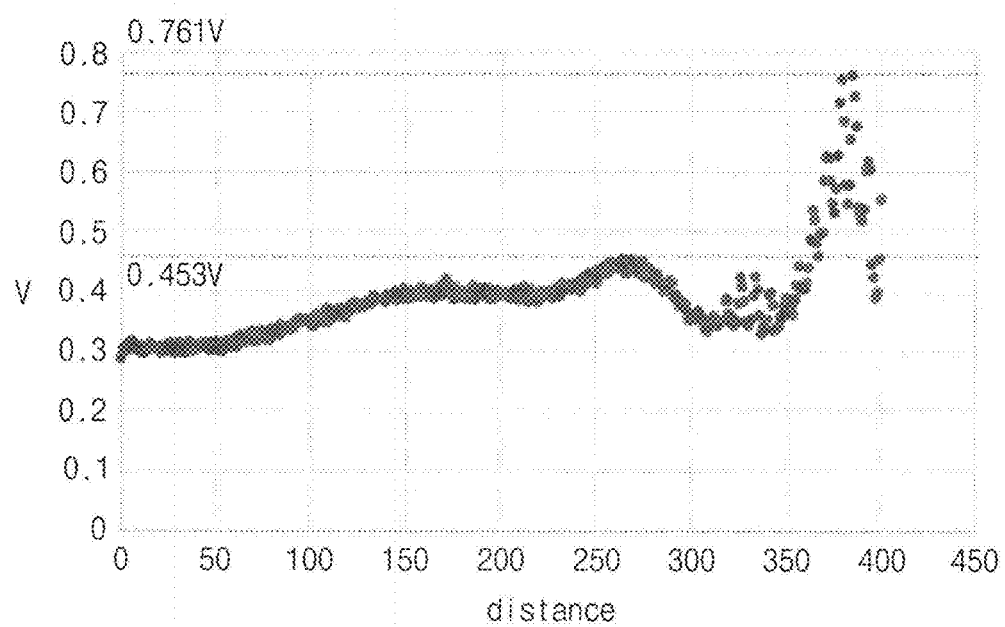
FIG. 5 is a graph showing the shape of the wave focused by the wave focusing device of FIG. 3.

FIG. 5 is a graph showing the shape of the wave focused by the wave focusing device of FIG. 3.

Referring to FIG. 5, the wave passing through the wave focusing lens 300 is focused at about 3.8 mm due to the phase overlapping, and has an intensity of about 0.761V.

According to the present example embodiments, the plurality of filters is overlapped with each other, to increase the wave focusing in the entire area near the surface.

In addition, the wave focusing is increased at the position corresponding to the center of each of the filters.

In addition, the plurality of filters is used, to pull the focal distance, compared that a single filter is used.

Although the exemplary embodiments of the present invention have been described, it is understood that the present invention should not be limited to these exemplary embodiments but various changes and modifications can be made by one ordinary skilled in the art within the spirit and scope of the present invention as hereinafter claimed.

What is claimed is:

1. An ultrasonic lens, comprising:
a plate filter having a plurality of overlapping filter patterns defined by perforations through the plate filter, the plate filter being configured to, in response to receiving a first ultrasonic wave having a first focal distance emitted by an ultrasonic wave emitter, output a second ultrasonic wave having a second focal distance less than the first focal distance by focusing the first ultrasonic wave by way of a phase overlap caused by diffracting the first ultrasonic wave based on the plurality of overlapping filter patterns,
wherein
the first focal distance extends from an output end of the ultrasonic wave emitter,
the second focal distance extends from an output end of the plate filter,
the plurality of overlapping filter patterns comprises:
a first filter pattern;
a second filter pattern overlapping the first filter pattern;
a third filter pattern overlapping the second filter pattern; and
additional filter patterns overlapping at least one of the first to third filter patterns, the first to third filter patterns extend along a first direction, and
a direction in which the additional filter patterns extend from the second filter pattern is different from the first direction.

2. The ultrasonic lens of claim 1, wherein a first portion of the second filter pattern is symmetrical to a second portion of the second filter pattern, with respect to a first axis through a center of the second filter pattern.

3. The ultrasonic lens of claim 1, wherein the plate filter is a Fresnel zone plate filter.

4. An ultrasonic wave emitting device, comprising:
a wave emitter configured to emit a first ultrasonic wave having a first focal distance extending from an output end of the wave emitter; and
a plate filter having a plurality of overlapping filter patterns defined by perforations through the plate filter, the plate filter being configured to, in response to receiving the first ultrasonic wave having the first focal distance emitted by the ultrasonic wave emitter, output a second ultrasonic wave having a second focal distance less than the first focal distance by focusing the first ultrasonic wave by way of a phase overlap caused by diffracting the first ultrasonic wave based on the plurality of overlapping filter patterns,
wherein
the plurality of overlapping filter patterns comprises:
a first filter pattern;
a second filter pattern overlapping the first filter pattern;
a third filter pattern overlapping the second filter pattern; and
additional filter patterns overlapping at least one of the first to third filter patterns, the first to third filter patterns extend along a first direction, and
a direction in which the additional filter patterns extend from the second filter pattern is different from the first direction.

5. The ultrasonic wave emitting device of claim 4, further comprising:
a first spacer between the wave emitter and the plate filter; and
a second spacer on a side of the plate filter opposite to the first spacer with the plate filter being between the first spacer and the second spacer,
wherein the first spacer comprises a first waveguide configured to communicate the first ultrasonic wave emitted by the wave emitted to the plate filter,
and the second spacer comprises a second waveguide configured to receive the second ultrasonic wave output by the plate filter.

6. The ultrasonic wave emitting device of claim 5, wherein the first waveguide comprises a first transparent material and the second waveguide comprises a second transparent material.

7. The ultrasonic waveguide emitting device of claim 6, wherein the first transparent material is the same as the second transparent material.

8. The ultrasonic waveguide emitting device of claim 6, wherein the first transparent material is the different from the second transparent material.

9. The ultrasonic waveguide emitting device of claim 5, wherein
the first waveguide has a first length extending from an input side facing the wave emitter to an output side facing the plate filter,
the second waveguide has a second length extending from an input side facing the plate filter to an output side facing away from the plate filter, and
the first length is different from the second length.

10. The ultrasonic waveguide emitting device of claim 9, wherein the first length is greater than the second length.

11. The ultrasonic waveguide emitting device of claim 9, wherein
the second length of the second spacer is less than the second focal distance of the second ultrasonic wave output by the plate filter.

12. The ultrasonic waveguide emitting device of claim 4, wherein a first portion of the second filter pattern is symmetrical to a second portion of the second filter pattern with respect to a first axis through a center of the second filter pattern.

13. The ultrasonic waveguide emitting device of claim 12, wherein
the second filter pattern has a primary opening at the center of the second filter pattern larger than one or more other openings in the second filter pattern,
each of the first filter pattern, the third filter pattern, the fourth filter pattern, the fifth filter pattern, the sixth filter pattern, and the seventh filter pattern has a corresponding primary opening at a corresponding center of each of the first filter pattern, the third filter pattern, the fourth filter pattern, the fifth filter pattern, the sixth filter pattern, and the seventh filter pattern larger than one or more other openings in each of the first filter pattern, the third filter pattern, the fourth filter pattern, the fifth filter pattern, the sixth filter pattern, and the seventh filter pattern, and
the primary opening in each of the each of the first filter pattern, the second filter pattern, the third filter pattern, the fourth filter pattern, the fifth filter pattern, the sixth filter pattern, and the seventh filter pattern facilitates the diffracting of the first ultrasonic wave and output of the second ultrasonic wave.

14. The ultrasonic waveguide emitting device of claim 12, wherein the plate filter has a quantity of focuses equal to a quantity of primary openings the plurality of filter patterns.

15. The ultrasonic waveguide emitting device of claim 4, wherein the plate filter has a quantity of focuses equal to a quantity of the plurality of filter patterns.

16. The ultrasonic lens of claim 2, wherein
the second filter pattern has a primary opening at the center of the second filter pattern larger than one or more other openings in the second filter pattern,
each of the first filter pattern, the third filter pattern, the fourth filter pattern, the fifth filter pattern, the sixth filter pattern, and the seventh filter pattern has a corresponding primary opening at a corresponding center of each of the first filter pattern, the third filter pattern, the fourth filter pattern, the fifth filter pattern, the sixth filter pattern, and the seventh filter pattern larger than one or more other openings in each of the first filter pattern, the third filter pattern, the fourth filter pattern, the fifth filter pattern, the sixth filter pattern, and the seventh filter pattern, and
the primary opening in each of the each of the first filter pattern, the second filter pattern, the third filter pattern, the fourth filter pattern, the fifth filter pattern, the sixth filter pattern, and the seventh filter pattern facilitates the diffracting of the first ultrasonic wave and output of the second ultrasonic wave.

17. The ultrasonic lens of claim 16, wherein the plate filter has a quantity of focuses equal to a quantity of primary openings the plurality of filter patterns.

18. The ultrasonic lens of claim 1, wherein the plate filter has a quantity of focuses equal to a quantity of the plurality of filter patterns.

19. The ultrasonic lens of claim 1, wherein a shape of each of the second and third filter patterns is identical to that of the first filter pattern, and a shape of each of the additional filter patterns is identical to that of the first filter pattern.

20. The ultrasonic lens of claim 1, wherein the additional filter patterns comprises:
a fourth filter pattern overlapping the first and second filter patterns;
a fifth filter pattern overlapping the second, third and fourth filter patterns;
a sixth filter pattern overlapping the first and second filter patterns; and
a seventh filter pattern overlapping the second, third and sixth filter patterns, and
wherein the second filter pattern is at a center of an arrangement of the plurality of the overlapping filter patterns in the plate filter.

* * * * *